United States Patent
Nguyen et al.

(10) Patent No.: US 10,545,129 B2
(45) Date of Patent: Jan. 28, 2020

(54) ESTIMATING A RESERVE OF A RESERVOIR

(71) Applicant: Halliburton Energy Services, Inc., Houston, TX (US)

(72) Inventors: Phillip D. Nguyen, Houston, TX (US); Loan K. Vo, Houston, TX (US); Bradley J. Sparks, Richmond, TX (US); David Loveless, Houston, TX (US); Douglas Everett Wyatt, Kingwood, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 318 days.

(21) Appl. No.: 15/309,054

(22) PCT Filed: Aug. 5, 2014

(86) PCT No.: PCT/US2014/049792
§ 371 (c)(1),
(2) Date: Nov. 4, 2016

(87) PCT Pub. No.: WO2016/022106
PCT Pub. Date: Feb. 11, 2016

(65) Prior Publication Data
US 2017/0074852 A1   Mar. 16, 2017

(51) Int. Cl.
*G01N 33/28* (2006.01)
*E21B 49/08* (2006.01)
(Continued)

(52) U.S. Cl.
CPC ......... *G01N 33/2823* (2013.01); *E21B 49/08* (2013.01); *G01N 23/046* (2013.01); *G01N 24/081* (2013.01)

(58) Field of Classification Search
CPC .. G01N 1/28; G01N 3/12; G01N 1/00; G01N 33/24; G01N 33/2823; G01N 24/081; G01M 3/02; E21B 49/08
USPC ........................................ 73/37, 152.46, 863
See application file for complete search history.

(56) References Cited

U.S. PATENT DOCUMENTS

| | | | |
|---|---|---|---|
| 4,649,483 A | | 3/1987 | Dixon |
| 5,291,796 A | * | 3/1994 | Schultz .................. E21B 49/081 |
| | | | 73/863 |

(Continued)

OTHER PUBLICATIONS

Rietz, D. C., & Usmani, A. H. (Jan. 1, 2007). Case Studies Illustrating the Use of Reservoir Simulation Results in the Reserves Estimation Process. Society of Petroleum Engineers. doi:10.2118/110066-MS.

(Continued)

*Primary Examiner* — Peter J Macchiarolo
*Assistant Examiner* — Mohammed E Keramet-Amircolai
(74) *Attorney, Agent, or Firm* — Haynes and Boone, LLP (57) ABSTRACT

A method and apparatus that includes isolating a sample having a known volume and obtained near a reservoir that has a reserve; extracting hydrocarbons from the sample; and identifying data associated with the hydrocarbons. The data may include the volume of the extracted hydrocarbons. The method also includes using the data to estimate the reserve of the reservoir. The method can also include pulverizing the sample to release additional hydrocarbons.

26 Claims, 6 Drawing Sheets

(51) Int. Cl.
 *G01N 23/046* (2018.01)
 *G01N 24/08* (2006.01)

(56) References Cited

U.S. PATENT DOCUMENTS

| | | | | |
|---|---|---|---|---|
| 5,299,453 | A * | 4/1994 | Sprunt | G01N 15/0893 436/31 |
| 2002/0134587 | A1 * | 9/2002 | Rester | E21B 47/10 175/48 |
| 2004/0035199 | A1 * | 2/2004 | Meister | E21B 47/01 73/152.46 |
| 2004/0054478 | A1 | 3/2004 | Brygynevych | |
| 2004/0158406 | A1 | 8/2004 | Harrison | |
| 2005/0132775 | A1 * | 6/2005 | Laugharn, Jr. | B01L 3/505 73/12.01 |
| 2006/0129322 | A1 | 6/2006 | Macgregor et al. | |
| 2009/0248310 | A1 * | 10/2009 | Zuo | E21B 47/102 702/11 |
| 2011/0246143 | A1 * | 10/2011 | Pomerantz | E21B 49/00 703/2 |
| 2012/0266697 | A1 * | 10/2012 | Burisch | G01N 1/36 73/863 |
| 2014/0256055 | A1 * | 9/2014 | Pottorf | G01V 9/007 436/163 |
| 2015/0149089 | A1 * | 5/2015 | Cespedes | E21B 49/00 702/2 |
| 2016/0376885 | A1 * | 12/2016 | Li | E21B 43/00 702/12 |

OTHER PUBLICATIONS

Harrell, R., Gajdica, R., Elliott, D., Ahlbrandt, T. S., & Khurana, S. (Jan. 1, 2005). Panel: Oil and Gas Reserve Estimates. Offshore Technology Conference. doi:10.4043/17714-MS.

Cheng, Y., Lee, W. J., & McVay, D. A. (Jan. 1, 2007). Improving Reserves Estimates From Decline Curve Analysis of Tight and Multilayer Gas Wells. Society of Petroleum Engineers. doi:10.2118/108176-MS.

Denney, D. (Dec. 1, 2010). Gas-Reserves Estimation in Resource Plays. Society of Petroleum Engineers. doi:10.2118/1210-0065-JPT.

International Search Report and Written Opinion issued by the Korean Intellectual Property Office regarding International Application No. PCT/US2014/049792 dated May 1, 2015, 13 pages.

Zendehboudi et al., Connectionist model to estimate performance of reservoirs: enhanced oil recovery implications, Industrial & Engineering Chemistry Research, 2014, vol. 53, No. 4, pp. 1645-1662 (Published on Dec. 2, 2013).

Cheng et al., Quantification of uncertainty in reserve estimate from decline curve analysis of production data for unconventional reservoirs, Journal of Energy resources Technology, 2008, vol. 130, No. 4, 043201, pp. 1-5.

Withjack, et al., Characterization and saturation determination of reservoir metagraywacke from The Geysers corehole SB-15-D (USA), using Nuclear Magnetic Resonance Spectrometry and X-ray Computed Tomography, Geothermics, vol. 30, Issues 2-3, Apr. 2001, pp. 255-268.

* cited by examiner

ESTIMATING A RESERVE OF A RESERVOIR

TECHNICAL FIELD

The present disclosure relates generally to estimating a reserve of a reservoir, especially unconventional reservoirs such those located within a shale play.

BACKGROUND

An estimate of a reserve of hydrocarbons in a reservoir is used in a variety of ways, such as in economic analyses, equipment and production planning, etc. Typically, the reserve estimates are calculated using rate-time decline relations, pressure decline curves, or formation average porosity, with the estimates often being significantly greater than or less than the actual reserve in the reservoir. Often, the reserve estimates are calculated using data obtained while the well is producing. Inaccurate estimates are common when the reservoir is an unconventional reservoir, such as one that is located in a shale play.

The present disclosure is directed to a method of estimating a reserve of a reservoir that overcomes one or more of the shortcomings in the prior art.

BRIEF DESCRIPTION OF THE DRAWINGS

Various embodiments of the present disclosure will be understood more fully from the detailed description given below and from the accompanying drawings of various embodiments of the disclosure. In the drawings, like reference numbers may indicate identical or functionally similar elements.

DETAILED DESCRIPTION

Illustrative embodiments and related methods of the present disclosure are described below as they might be employed in a method of estimating a reserve of a reservoir. In the interest of clarity, not all features of an actual implementation or method are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methods of the disclosure will become apparent from consideration of the following description and drawings.

The foregoing disclosure may repeat reference numerals and/or letters in the various examples. This repetition is for the purpose of simplicity and clarity and does not in itself dictate a relationship between the various embodiments and/or configurations discussed. Further, spatially relative terms, such as "beneath," "below," "lower," "above," "upper," "uphole," "downhole," "upstream," "downstream," and the like, may be used herein for ease of description to describe one element or feature's relationship to another element(s) or feature(s) as illustrated in the figures. The spatially relative terms are intended to encompass different orientations of the apparatus in use or operation in addition to the orientation depicted in the figures. For example, if the apparatus in the figures is turned over, elements described as being "below" or "beneath" other elements or features would then be oriented "above" the other elements or features. Thus, the exemplary term "below" may encompass both an orientation of above and below. The apparatus may be otherwise oriented (rotated 90 degrees or at other orientations) and the spatially relative descriptors used herein may likewise be interpreted accordingly.

Figure 1:
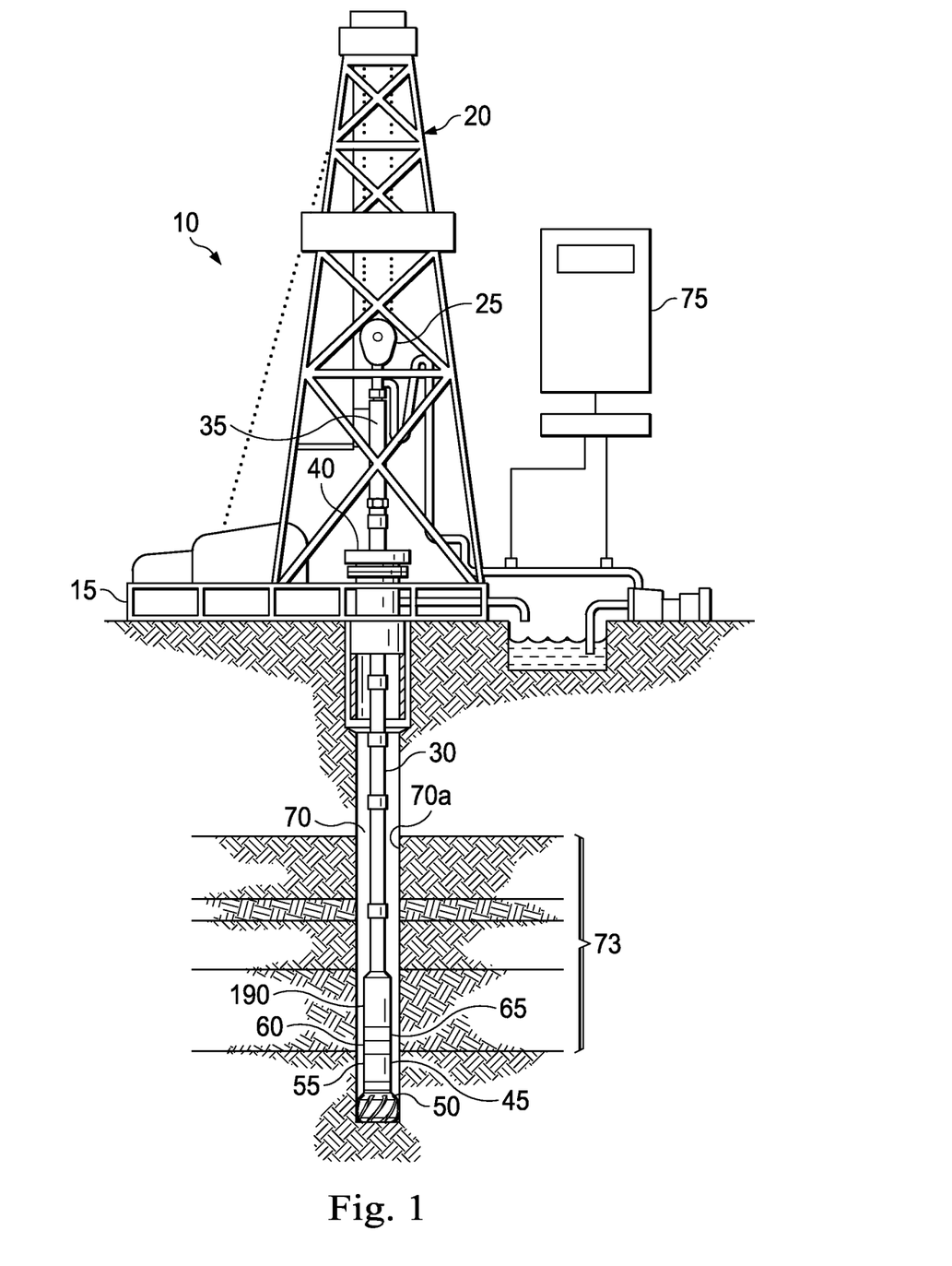
FIG. 1 is a schematic illustration of an oil and gas rig operably coupled to a bottom hole assembly.

Referring initially to FIG. 1, a drilling rig is schematically illustrated and generally designated 10. A drilling platform 15 that is equipped with a derrick 20 supports a hoist 25 for raising and lowering a drill string 30. The hoist 25 suspends a top drive 35 suitable for rotating the drill string 30 and lowering it through a well head 40. Connected to the lower end of the drill string 30 is the bottom hole assembly (BHA) 45. The BHA 45 may include a drill bit 50; a mud motor 55; a measurement tool such as, for example, a measurement while drilling (MWD)/logging while drilling (LWD) system 60; and a telemetry system 65.

As the drill bit 50 rotates, it creates a bore hole 70 having a bore hole wall 70*a* that passes through various formations 73 and through a reservoir of hydrocarbons present in the various formations 73. The mud motor 55 and/or the system 60 communicates with a surface system 75 through the use of the telemetry system 65 such as, for example, a mud pulse, an electromagnetic, an acoustic, a torsion, or a wired drill pipe telemetry system.

Finally, FIG. 1 illustrates a reservoir reserve estimator system 80 used to estimate hydrocarbon reserves in the formations 73. All or a portion of the reservoir reserve estimator system 80 may be adjacent or in proximity to the drilling rig 10 or may be remotely located with respect to the drilling rig 10.

Even though FIG. 1 depicts a vertical wellbore, it should be understood by those skilled in the art that the apparatus according to the present disclosure is equally well suited for use in wellbores having other orientations including horizontal wellbores, slanted wellbores, multilateral wellbores or the like. Also, even though FIG. 1 depicts an onshore operation, it should be understood by those skilled in the art that the apparatus according to the present disclosure is equally well suited for use in offshore operations. Finally, while FIG. 1 depicts a top drive drilling rig utilized with conventional drill pipe as the drillstring, the apparatus of the present disclosure is not limited a particular type of drilling rig or drillstring.

Figure 2:
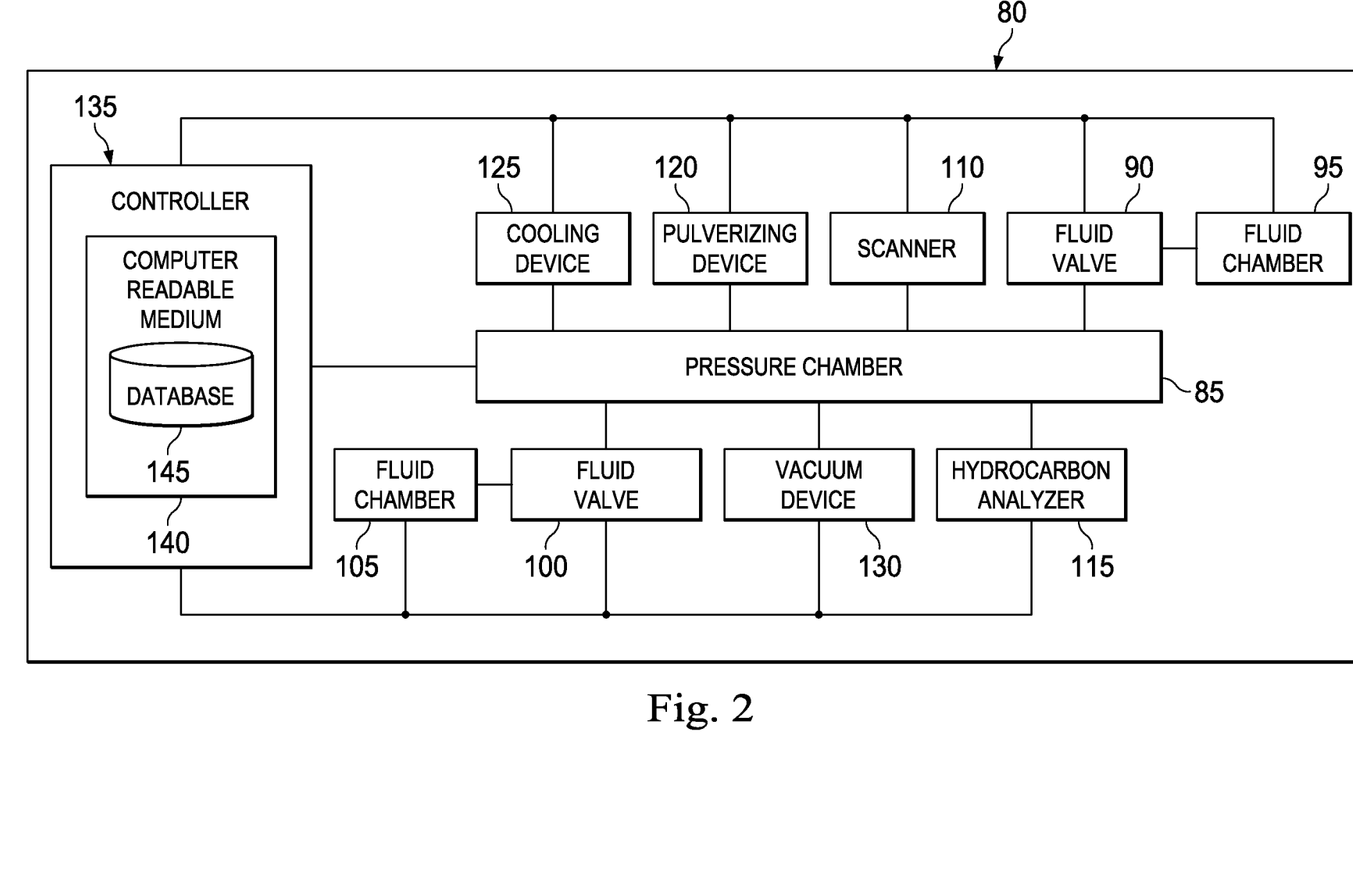
FIG. 2 is a diagrammatic illustration of a portion of a reservoir reserve estimating assembly, according to some embodiments.

In one or more exemplary embodiments and as shown in FIG. 2, the reservoir reserve estimator system 80 generally includes a pressure chamber 85 that is sized to accommodate a formation sample. In one or more exemplary embodiments, the sample may be a core sample or a core plug. In one or more exemplary embodiments, a reservoir pressure is present such that the sample is exposed to the reservoir pressure while downhole. In one or more exemplary embodiments, the system 80 may also include a fluid valve 90 that controls the flow of a fluid through a fluid line (not shown) that fluidically couples a fluid chamber 95 to the pressure chamber 85. Additionally, and in one or more embodiments, the system 80 may include a fluid valve 100 that controls the flow a fluid, such as a gas, through a fluid line (not shown) that fluidically couples a fluid chamber 105 to the pressure chamber 85. In one or more exemplary embodiments, the system 80 may also include a scanner 110 that is disposed in proximity to the pressure chamber 85 in order to scan the sample that is accommodated in the pressure chamber 85. In one or more exemplary embodiments, the system 80 may also include a hydrocarbon analyzer 115 that is disposed in proximity to the pressure chamber 85 such that hydrocarbons extracted from the sample may be evaluated by the hydrocarbon analyzer 115. In one or more embodiments, the system 80 also may include: a fracturing or pulverizing device 120 disposed in proximity to the pressure chamber 85; a cooling device 125 disposed in proximity to the pressure chamber; and/or a vacuum device 130 disposed in proximity to the pressure chamber 85. In one or more exemplary embodiments, the vacuum device 130 is capable of lowering the pressure within the pressure chamber 85 and/or increasing the pressure within the pressure chamber 85. In one or more embodiments, the system 80 also may include a controller 135 in communication with one or more of the pressure chamber 85, the fluid valves 90 and 100, the fluid chambers 95 and 105, the scanner 110, the hydrocarbon analyzer 115, the pulverizing device 120, the cooling device 125, and the vacuum device 130. The controller 135 also includes a computer readable medium 140 operably coupled thereto. Instructions accessible to, and executable by, the controller 135 are stored on the computer readable medium 140. In one or more embodiments, a database 145 is also stored in the computer readable medium 140. In one or more exemplary embodiments, data is stored in the database 145. In one or more exemplary embodiments, the data stored in the database 145 may include: data relating to the type of fluid stored in the fluid chambers 95 and/or 105; data relating to rock lithology, porosity, clay content, etc. as a function of depth; and data relating to depth, time, temperature(s), volume, oil/gas type, water content, geographical response, permeability, porosity and lithology etc. However, a variety of other data may also be stored in the database 145. In one or more exemplary embodiments, the controller 135 controls functions of one or more of the pressure chamber 85, the fluid valves 90 and 100, the fluid chambers 95 and 105, the scanner 110, the hydrocarbon analyzer 115, the pulverizing device 120, the cooling device 125, and the vacuum device 130.

Figure 3:
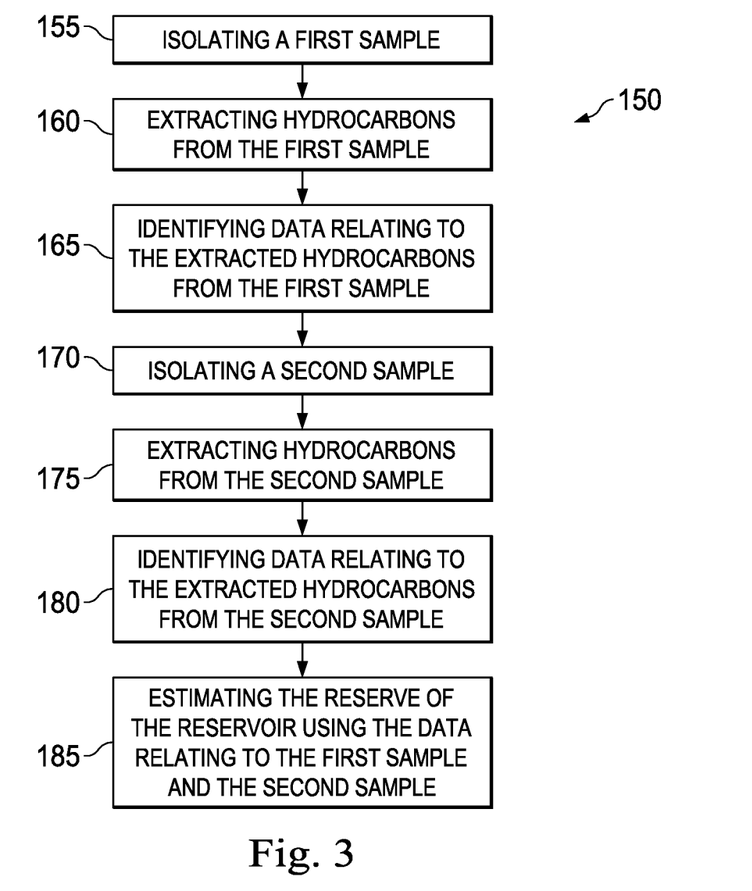
FIG. 3 is a flow chart illustration of a method of estimating a reserve of a reservoir, according to an exemplary embodiment of the present disclosure.

With reference to FIG. 3 with continuing reference to FIGS. 1-2, in one or more embodiments, a method of estimating the reserve of a reservoir is generally referred to by the reference numeral 150 and may include isolating a first sample at step 155, extracting hydrocarbons from the first sample at step 160, identifying data relating to the extracted hydrocarbons from the first sample at step 165, isolating a second sample at step 170, extracting hydrocarbons from the second sample at step 175, identifying data relating to the extracted hydrocarbons from the second sample at step 180, and estimating the reserve of a reservoir using the data relating to the first sample and the second sample at step 185. In one or more exemplary embodiments, the method 150 is a method of operating the system 80.

At the step 155, the first sample is isolated. In one or more exemplary embodiments, isolating the first sample includes placing the sample in a container (not shown) that is at least partially filled with a fluid, such as an inert fluid. In one or more embodiments, the container may be a structure sized to submerge or at least partially submerge the first sample in the inert fluid. Additionally, the container may also be open (not sealed) such that an extracted fluid, such as a hydrocarbon, may exit the container. In one or more embodiments, the inert fluid may be brine or oil, however a variety of mixtures and solutions are contemplated here. The first sample, the container, and the inert fluid then may be placed in the pressure chamber 85. In one or more exemplary embodiments, the sample is maintained at the reservoir pressure prior to the step 155. In one or more exemplary embodiments, the sample is maintained at a pressure range between 90% and 110% of the reservoir pressure prior to the step 155. That is, the sample is maintained at the reservoir pressure or at a percentage of the reservoir pressure while the sample is transported from a location downhole and to the pressure chamber 85. Therefore, in one or more exemplary embodiments, the sample may be accommodated within a pressurized vessel or capsule (not shown) to maintain the sample at the reservoir pressure. In one or more exemplary embodiments, maintaining the sample at or near the reservoir pressure allows for testing of the sample near downhole conditions to estimate how the formations 73 will react to additional drilling operations, completion operations, and/or production operations. In one or more exemplary embodiments, the pressurized sample that is accommodated within the capsule may be placed in the container, and the pressurized sample, capsule, and container may then be placed in the pressure chamber 85 at the step 155. In one or more embodiments, the first sample corresponds to a shale formation.

Figure 4:
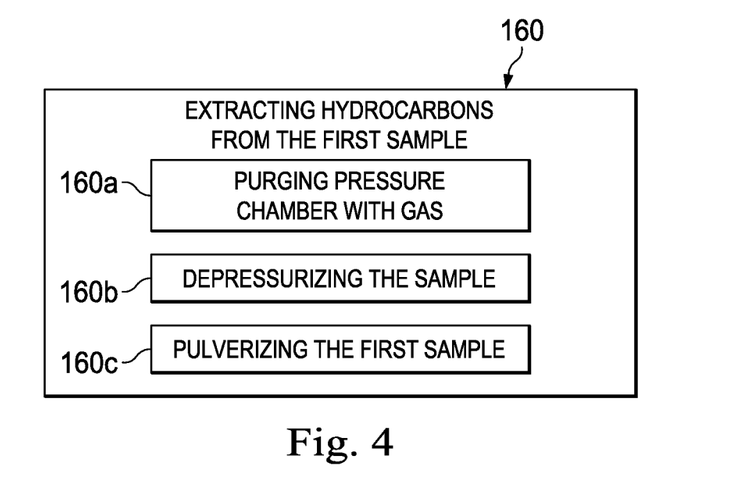
FIG. 4 is a flow chart illustration of a step of the method of FIG. 3 according to an exemplary embodiment of the present disclosure.

At the step 160, hydrocarbons are extracted from the first sample. In one or more exemplary embodiments and as shown in FIG. 4, extracting hydrocarbons from the first sample includes one or more of the sub-steps of purging the pressure chamber 85 with a gas at step 160a, depressurizing the sample at step 160b, and pulverizing the first sample at step 160c. At step 160a, the pressure chamber 85 is purged with the gas. In one or more exemplary embodiments, the gas is an inert gas, such as for example, nitrogen or argon. However, any type of inert gas may be used. In one or more exemplary embodiments, purging the pressure chamber 85 includes opening the fluid valve 90 such that the purging fluid may flow from the fluid chamber 95 to the pressure chamber 85. At step 160b, the sample is depressurized. In one or more example embodiments and when the sample is not maintained at the reservoir pressure, the pressure within the pressure chamber 85 is lowered to depressurize the sample. In one or more exemplary embodiments, the pressure within the pressure chamber 85 is lowered to a range of between about −3 atm to 3 atm. In one or more embodiments, lowering the pressure within the pressure chamber 85 includes activating the vacuum device 130 to reduce the pressure within the pressure chamber 85 to extract hydrocarbons, such as a gas, that are present within the first sample from the first sample and through the inert fluid. In one or more exemplary embodiments and when the sample is accommodated within the capsule, the vacuum device 130 increases the pressure within the pressure chamber 85 to the reservoir pressure or to a range between about 90% to 110% of the reservoir pressure. In one or more exemplary embodiments, increasing the pressure within the pressure chamber 85 is dependent on the reservoir pressure from where the sample is acquired. Accordingly, the pressure will depend on the lithostatic, hydrostatic, pore and any localized dynamic pressures. After the pressure within the pressure chamber 85 is increased, the capsule may then be opened during the step 160 such that the sample is exposed to the pressure within the pressure chamber 85 and or exposed to the fluid within the pressure chamber 85. In one or more exemplary embodiments, the pressure within the pressure chamber 85 is then lowered to aid in extracting hydrocarbons from the sample. At the step 160c, the pulverizing device 120 pulverizes, or fractures, the first sample. In one or more embodiments, the pulverizing device 120 may include a device that produces an acoustic sonic wave such that the vibrations cause the first sample to be pulverized. However, the pulverizing device 120 may include other crushing, grinding or pulverizing mechanisms, such as hammers, a hammer mill, a grinding mill, other types of mills, or projectiles, such as a plurality of stainless steel balls, that interact with the first sample until the first sample breaks or is pulverized. In one or more embodiments, the sub-step 160c is performed simultaneously with the sub-step 160b. However, the sub-step 160c may be performed prior to or after the sub-step 160b. Pulverizing the first sample generally increases the surface area of the first sample, which may increase the rate at which hydrocarbons are extracted from the first sample. Additionally, pulverizing the first sample may increase the volume of hydrocarbons that are extracted. Thus, pulverizing the first sample while a vacuum force is applied to the first sample may increase the extraction rate of the hydrocarbons and the volume of the extracted hydrocarbons. In one or more exemplary embodiments and when the sample is associated with an unconventional reservoir, hydrocarbons are captured in areas other than the pore spaces of the sample. Therefore, pulverizing the sample releases hydrocarbons from the sample. Thus, and in one or more exemplary embodiments, the volume of the extracted hydrocarbons reflects a maximum available volume of extracted hydrocarbons that can be released from the sample. In one or more exemplary embodiments, one or more of the sub-steps of the step 160 may recreate or otherwise simulate a downhole operation or an activity that is performed downhole. For example, one of the sub-steps of the step 160 may simulate the downhole operation of hydraulic fracturing. In another example, one of the sub-steps of the step 160 may simulate the downhole operation of pumping hydrocarbons from the reservoir.

At the step 165, data relating to the hydrocarbons extracted from the first sample is identified. In one or more embodiments, the hydrocarbon analyzer 115 is a gas chromatography ("GC") column that is disposed proximate the container such that the extracted hydrocarbons pass through the GC column. However, the hydrocarbon analyzer 115 may also be or include a mass spectrometer, a Headspace gas chromatography-mass spectrometry ("Headspace GC/MS") or a Pyrolysis-gas chromatography-mass spectrometry ("Pyrolysis GC/MS") or other types of gas chromatography-mass spectrometry; an acoustic sensor; a microacoustic sensor; an optical sensor, such as a multivariate or integrated computational optical element; an x-ray; and/or an electrical sensor. In one or more exemplary embodiments, the hydrocarbon analyzer 115 may be located near or in a hood, a vent, or other device that may be located near or around the container to capture the extracted hydrocarbons. Alternatively, the extracted hydrocarbons may be collected in a "trap" comprising of liquid nitrogen and dissolved in a solvent. However, the trap may involve any variety of liquids. The analysis of the extracted hydrocarbons may include obtaining data relating to the volume of the extracted hydrocarbons, obtaining data relating to an extracted hydrocarbon to sample volume ratio (i.e., the hydrocarbon saturation ratio), determining the composition of the hydrocarbons, determining porosity data, determining X-ray diffraction ("XRD") data, determining clay content data, determining the residual oil in place, determining the irreducible water saturation, determining the produced water volume, etc. In one or more exemplary embodiments, the volume of the extracted hydrocarbons is used to calculated the hydrocarbon saturation ratio. The hydrocarbon saturation ratio is a ratio of the volume of extracted hydrocarbons per sample to the volume of the sample.

The steps 155, 160, and 165 are repeated for a second and any subsequent samples in order to isolate a sample, extract hydrocarbons from the sample, and identify data relating to the extracted hydrocarbons from the sample. That is, at the step 170, a second sample is isolated. Isolating the second sample at the step 170 is substantially similar to isolating the first sample at the step 155 and therefore will not be described further here. However, the second sample may represent one of the various formations 73 obtained at a depth different from a depth associated with the first sample. Alternatively, the second sample may be associated with one of the various formations 73 obtained at a depth identical to the first sample, but from a different multilateral wellbore extending from the wellbore 70. In other words, a first sample may be taken at a predetermined depth from a first multilateral wellbore extending from a main wellbore 70 and a second sample may be taken at the predetermined from a second multilateral wellbore extending from main wellbore 70 to provide data relating to the formation at the particular depth across a hydrocarbon reservoir. Alternatively, the second sample may be associated with one of the various formations 73 obtained at a depth identical to the first sample, but at a lateral location different from the lateral location of the first sample. For example, in "horizontal drilling", the depth of the wellbore 70 may not increase as the wellbore 70 extends in the lateral direction. Accordingly, multiple samples may be obtained at one depth but at different lateral locations. Regardless, the second sample is generally either: associated with a different wellbore from the first sample; associated with a different depth within the same wellbore as the first sample; or associated with a different lateral location within the same wellbore as the first sample. In one or more embodiments, the second sample corresponds to a shale formation.

At the step 175, hydrocarbons are extracted from the second sample. Extracting hydrocarbons from the second sample at the step 175 is substantially similar to extracting hydrocarbons from the first sample at the step 160 and therefore will not be described further here.

At the step 180, data relating to the hydrocarbons extracted from the second sample is identified. Identifying data relating to the hydrocarbons extracted from the second sample at the step 180 is substantially similar to identifying data relating to the hydrocarbons extracted from the first sample the step 165 and therefore will not be described further here.

At the step 185, a reserve of the reservoir estimate is created using the data relating to the first sample and the second sample. In one or more embodiments, the hydrocarbon saturation ratio of the first sample and the hydrocarbon saturation ratio of the second sample is used to create an average hydrocarbon saturation ratio. In one or more exemplary embodiment, the reserve of the reservoir estimate may be created by combining seismic data, depth intervals, areas of coverage, etc. Often, seismic data relates to the volume of the reservoir (an area of the reservoir and a depth of the reservoir). In one or more exemplary embodiment, the average hydrocarbon saturation ratio is used with the volume of the reservoir to create the reserve of the reservoir estimate. For example, the average hydrocarbon saturation ratio ((volume of extracted hydrocarbon)/(volume of sample)) may be multiplied by the volume of the reservoir to estimate the volume of the hydrocarbons within the reservoir, or the reserve of the reservoir estimate.

Figure 5:
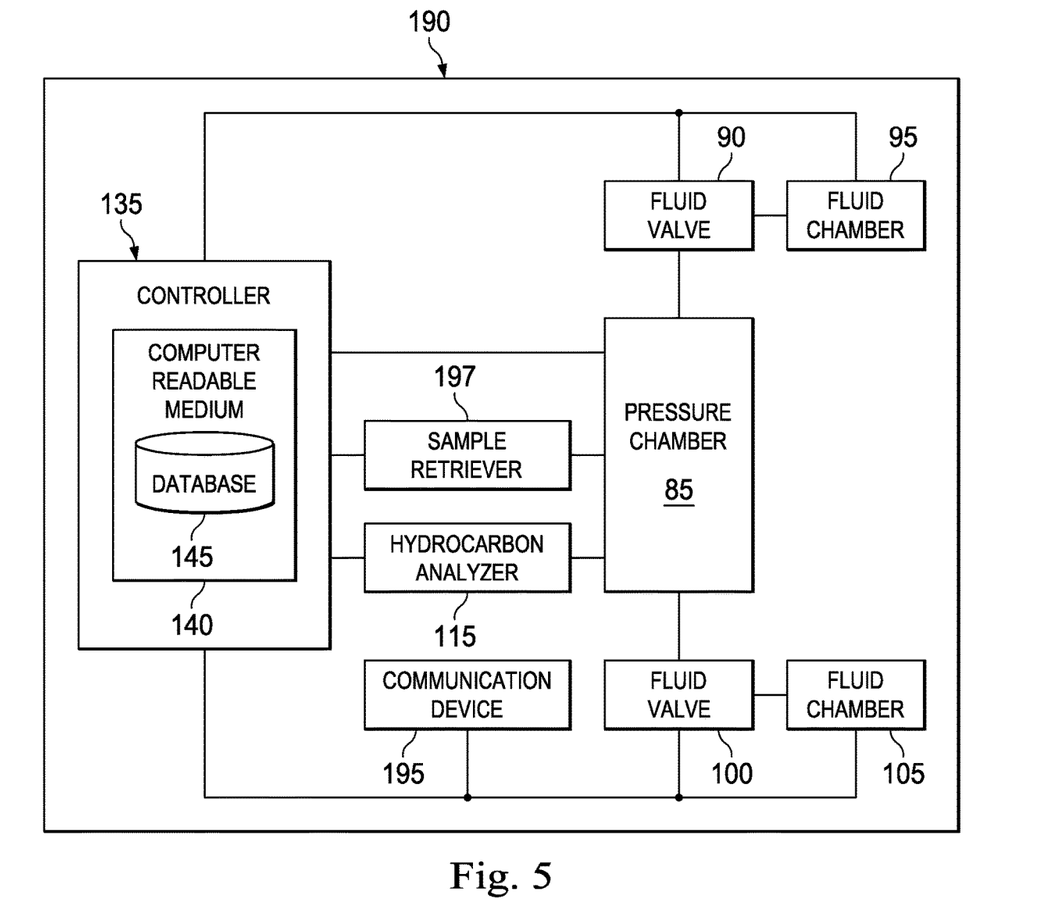
FIG. 5 is a diagrammatic illustration of a portion of a reservoir reserve estimation tool, according to an exemplary embodiment of the present disclosure.

Exemplary embodiments of the present disclosure may be altered in a variety of ways. For example, the system 80 may be a reservoir reserve estimation downhole tool 190 (shown in FIG. 1) such that all or a portion of the steps 155-185 occur while the tool 190 is downhole. In one or more embodiments, tool 190 includes an integrated computational element that can analyze reservoir samples in-situ. In one or more exemplary embodiments, the tool 190, as shown in FIG. 5, may also include a communication device 195 that communicates with other downhole tools and/or the surface system 75. The communication device 195 may be a wired drill pipe network. The wired drill pipe network permits one way or bi-directional communication with the surface system 75. In one or more embodiments, the tool 190 receives data or information such as, for example, the depth or location of the tool 190, etc. In one or more embodiments, the tool 190 includes a sample retriever 197. In one or more embodiments, the sample retriever 197 extends radially from the drill string 30 and towards the borehole wall 70a to obtain the first sample. In one or more exemplary embodiments, retrieval of the sample may occur while the drill string 30 is stationary. However, the retrieval of the sample may occur while the drill string 30 moves relative to the borehole wall 70a. Alternatively, the sample retriever 197 may be a cutting shoe that extends longitudinally relative to the drill string 30. In one or more exemplary embodiments, after the tool 190 has identified data relating to the extracted hydrocarbons from the first sample at the step 165, the sample is released from the pressure chamber 85 and the sample retriever 197 retrieves another sample to begin the step 170. In one or more embodiments, the tool 190 uses the communication device 195 to relay information relating to the first sample, the second sample, and/or the reserve of the reservoir estimate to the surface system 75. In one or more embodiments, the tool 190 is connectable to the drill string 30. In one or more exemplary embodiments, the tool 190 is or includes a Rotary Sidewall Coring Tool or RSCT™ available by Halliburton Energy Services, Inc. in Houston, Tex., USA. In one more exemplary embodiments, the tool 190 is or includes a CoreVault™ System available by Halliburton Energy Services, Inc. of Houston, Tex., USA. Alternatively, the tool 190 may be transportable, using a vehicle, from one drill site to another drill site so the method 150 or a portion of the method 150 may be performed in proximity to the drill rig 10.

Exemplary embodiments of the present disclosure may be altered in additional ways. For example, the first sample may be a crude-laden shale sample. In one or more exemplary embodiments, instead of submerging or partially submerging the first sample in the inert fluid, the first sample may be submerged or partially submerged in a solvent, such as for example a hydrocarbon-bearing solvent. For example, the solvent may be carbon disulfide or carbon tetrachloride. When pulverized, the amount or volume of hydrocarbon or crude extracted from the sample is used to create the reserve of the reservoir estimate. Additionally, during the step 160, the cooling device 125 may lower the temperature of the first sample through a range of temperatures including less than less than 32° Fahrenheit, less than 0° Fahrenheit, less than −50° Fahrenheit, or less than −100° Fahrenheit. In one or more embodiments, the cooling device 125 may be or include liquid nitrogen. In one or more exemplary embodiments, the solvent drives the solubility equilibrium of gaseous hydrocarbons out of the first sample and into the solvent. In general, lowering the temperature of the first sample increases the solubility of gaseous hydrocarbons in the solvent. Data relating to the extracted gaseous hydrocarbons or low molecular weight hydrocarbons may then be identified at the step 165.

Figure 6:
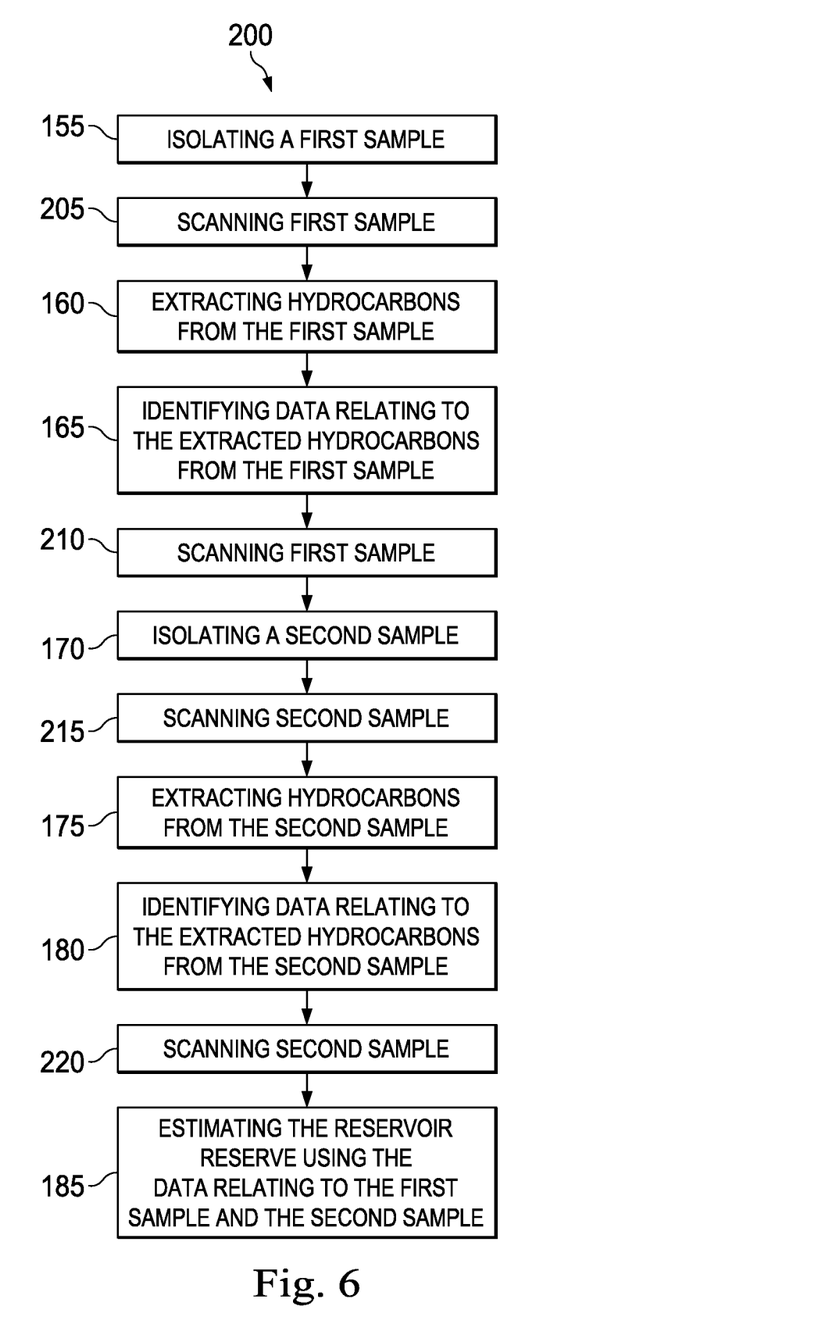
FIG. 6 is a flow chart illustration of another method of estimating a reserve of a reservoir, according to an exemplary embodiment of the present disclosure.

Exemplary embodiments of the present disclosure may be altered in a variety of ways. In one or more exemplary embodiments and as illustrated in FIG. 6, a method of estimating the reserve of the reservoir 200 is identical to the method 150 except the sub-step of 160c is omitted and instead, a step 205 and a step 210 of scanning the first sample and a step 215 and a step 220 of scanning the second sample is included, as described in more detail below. That is, the method 200 includes isolating a first sample at the step 155, scanning the first sample at the step 205, extracting hydrocarbons from the first sample at the step 160, identifying data relating to the extracted hydrocarbons from the first sample at the step 165, scanning the first sample at the step 210, isolating a second sample at the step 170, scanning the second sample at the step 215, extracting hydrocarbons from the second sample at the step 175, identifying data relating to the extracted hydrocarbons from the second sample at the step 180, scanning the second sample at the step 220, and estimating the reserve of a reservoir using the data relating to the first sample and the second sample at the step 185.

More specifically, after the step 155 and prior to the step 160, the method 200 includes scanning the first sample at the step 205. Generally, the scanner 110 performs a computed tomography "CT" scan or similar scan of the first sample. In one or more exemplary embodiments, the scanner 110 performs a nuclear magnetic resonance ("NMR") scan or an ultrahigh frequency acoustic scan. In one or more exemplary embodiments, the scanner 110 "looks" through the sample and digitally visualizes the internal matrix, crystalline, and macromolecular structure. In one or more embodiments, scanning the first sample at the step 205 can be used to determine an initial availability of pore structures of the first sample. In one or more exemplary embodiments, the results of the scan involve determining or identifying the pore-system (e.g., structure of pores, pore throats, and pore interconnectedness) of a sample such that the lithologically dependent reservoir permeability, produceability, and/or reserves may be identified. Generally, the results of the scan are more significant in high-permeability formations (e.g., sandstones) and less significant in a shale formation, since shale formations are associated with hydrocarbon adsorption.

After the step 165, the method 200 includes scanning the first sample a second time, at the step 210. Scanning the first sample at the step 210 is substantially identical to scanning the first sample at the step 205 and further detail will not be provided here. In one or more embodiments, the results of the scan of the first sample at the step 210 can be used to determine the extent of the inert oil invasion into the first sample and thus, the remaining untreated pore spaces in the first sample. That is, the results of the scan at the step 210 may be compared to the results of the scan at the step 205 to identify remaining untreated pore spaced and/or identify changes to the sample that occurred due to activities of the step 160. In one or more exemplary embodiments, the results of the scans can be compared to determine how a downhole operation would affect the formations 73 or affect the volume of extracted hydrocarbons. In one or more exemplary embodiments, the results of the scans can be compared to identify changes in the sample when the sample is exposed to different pressures. In one or more exemplary embodiments, the results of the scans can be compared to identify changes in the sample relating to the release or extraction of hydrocarbons.

After the step 170 and prior to the step 175, the method 200 includes scanning the second sample at the step 215. Scanning the second sample at the step 215 is substantially identical to scanning the first sample at the step 205 and further detail will not be provided here.

After the step 180, the method 200 includes scanning the second sample a second time, at the step 220. Scanning the second sample at the step 220 is substantially identical to scanning the first sample at the step 210 and further detail will not be provided here.

In one or more embodiments, the methods 150 and/or 200 may be used to estimate the reserve of the reservoir, or to create the reserve of the reservoir estimate, when the reservoir is an unconventional reservoir or a conventional reservoir. In one or more embodiments, an unconventional reservoir may include a hydrocarbon reservoir that has low permeability and porosity. In one or more exemplary embodiments, an unconventional reservoir may include tight-gas sands, coalbed methane, shale gas, shale oil, heavy oil and/or tar sands, methane hydrates, and gas-hydrate deposits. In one or more exemplary embodiments, a conventional reservoir is a reservoir that is not an unconventional reservoir. In one or more exemplary embodiments, a conventional reservoir is a reservoir in which the hydrocarbons flow readily into the wellbore 70. In one or more exemplary embodiments, a conventional reservoir may include sandstones or carbonates. In one or more embodiments, the methods 150 and/or 200 are performed prior to production operations associated with the reservoir, during production operations associated with the reservoir, and/or after production operations associated with the reservoir. Thus, the methods 150 and/or 200 may be used to determine if continued drilling operations are economically feasible for a specific reservoir and/or determine the remaining reserve of a reservoir that is already producing. In one or more exemplary embodiments, the methods 150 and/or 200 may be used to create the reserve of the reservoir estimate independently from data obtained during production operations (i.e., bringing hydrocarbons to the surface of the well in order to transport the hydrocarbons away from the well).

In one or more embodiments, the methods 150 and/or 200 are used to determine the reserve of the reservoir estimate based on data associated with hydrocarbons extracted from samples having known volumes. In one or more embodiments, the methods 150 and/or 200 use a measured extracted hydrocarbon volume per sample volume (i.e., the hydrocarbon saturation ratio) to estimate the reserve of the reservoir, or to create the reserve of the reservoir estimate. The methods 150 and/or 200 produces a rapid reserve estimate made at near reservoir conditions potentially under both a pre-fracture and post-fracture stimulation scenario. In one or more exemplary embodiments, the method 150 and/or 200 is used to create an estimate of an available (i.e., recoverable) reserve of the reservoir. For example, when one of the sub-steps of the step 160 involves simulating the downhole operation of hydraulic fracturing, the first data and/or the second data can be used to estimate of the available reserve of the reservoir when hydraulic fracturing is performed.

Generally, the accuracy of the reserve of the reservoir estimate increases with the number of samples used and tested. Thus, and in one or more exemplary embodiments, the steps 155-180 should be repeated until hydrocarbons have been extracted from twenty (20) or more samples, or in the case of a lesser amount, at least a plurality of samples, with the reserve of the reservoir estimate based on the analysis of the hydrocarbons extracted from the twenty samples. In one or more embodiments, the number of samples used in the methods 150 and/or 200 is greater than 10, greater than 20, greater than 30, greater than 40, or greater than 50.

Figure 7:
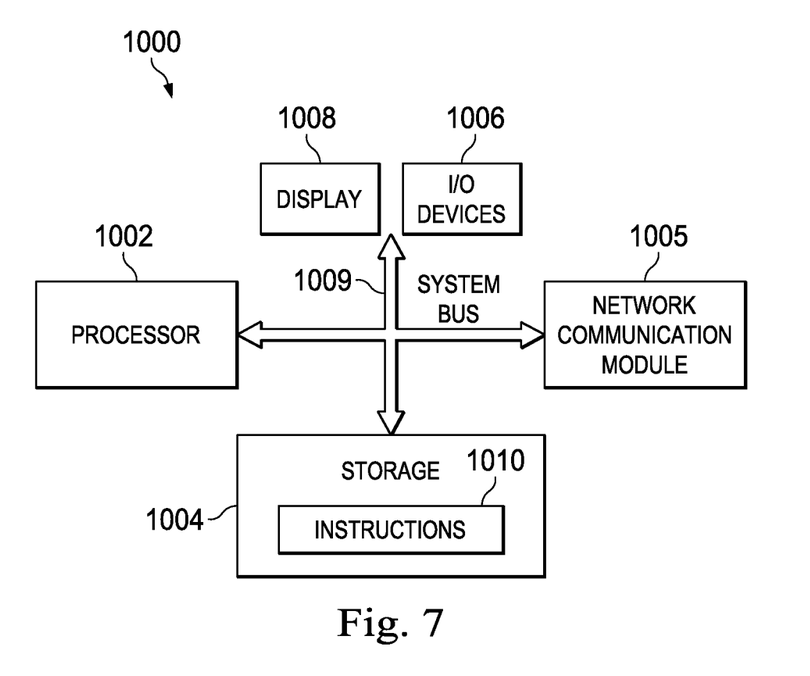
FIG. 7 is a block diagram of a computer system adapted for implementing a reservoir reserve estimating assembly, according to an exemplary embodiment of the present disclosure.

FIG. 7 is a block diagram of an exemplary computer system 1000 adapted for implementing the features and functions of the disclosed embodiments. In certain embodiments, the computer system 100 may be integrated locally with the reservoir reserve estimator system 80 and/or the tool 190 while in other embodiments the computer system 100 may be external from the reservoir reserve estimator system 80 and/or the tool 190. In one embodiment, the computer system 1000 includes at least one processor 1002, a non-transitory, computer-readable storage 1004, an optional network communication module 1005, optional I/O devices 1006, and an optional display 1008, and all interconnected via a system bus 1009. To the extent a network communications module 1005 is included, the network communication module 1005 is operable to communicatively couple the computer system 1000 to other devices over a network. In one embodiment, the network communication module 1005 is a network interface card (NIC) and communicates using the Ethernet protocol. In other embodiments, the network communication module 1005 may be another type of communication interface such as a fiber optic interface and may communicate using a number of different communication protocols. It is recognized that the computer system 1000 may be connected to one or more public (e.g. the Internet) and/or private networks (not shown) via the network communication module 1005. Software instructions 1010 executable by the processor 1002 for implementing the reservoir reserve estimator system 80 and/or the tool 190 in accordance with the embodiments described herein, may be stored in storage 1004. It will also be recognized that the software instructions 1010 may be loaded into storage 1004 from a CD-ROM or other appropriate storage media.

Thus, a method for estimating a reserve of a reservoir has been described. Embodiments of the method may generally include isolating a first sample associated with the reservoir; extracting a hydrocarbon from the first sample associated with the reservoir; identifying first data relating to the extracted hydrocarbon from the first sample; and estimating the reserve of the reservoir using the first data. In other embodiments, a method of estimating a reserve of a reservoir may generally include accommodating a sample obtained from a reservoir having a reserve in a pressure chamber; submerging at least a portion of the sample in a fluid; filling the pressure chamber with a gas; lowering the pressure within the pressure chamber to extract a hydrocarbon from the sample; identifying data relating to the extracted hydrocarbon; and estimating the reserve of the reservoir using the data relating to the extracted hydrocarbon. For any of the foregoing embodiments, the method may include any one of the following, alone or in combination with each other:

Isolating a second sample associated with the reservoir; extracting a hydrocarbon from a second sample associated with the reservoir; identifying second data relating to the extracted hydrocarbon from the second sample; and estimating the reserve of the reservoir using the first data and the second data.

Isolating the first sample comprises: submerging at least a portion of the first sample in a fluid; and disposing the first sample and the fluid in a pressure chamber; and wherein isolating the second sample comprises: submerging at least a portion of the second sample in the fluid; and disposing the second sample and the fluid in the pressure chamber.

Extracting a hydrocarbon from the first sample comprises: purging the pressure chamber with an inert gas; and applying a vacuum force to the first sample; and wherein extracting a hydrocarbon from the second sample comprises: purging the pressure chamber with the inert gas; and applying a vacuum force to the second sample.

Pulverizing the first sample and the second sample.

Pulverizing the first sample and the second sample comprises vibrating the first sample and the second sample.

Pulverizing the first sample and the second sample comprises striking the first sample and the second sample with a plurality of projectiles.

Scanning the first sample and the second sample before and after the hydrocarbons are extracted from the first sample and the second sample.

Lowering the temperature of the first sample and the second sample and wherein the fluid is a solvent.

The reservoir is an unconventional reservoir.

The reservoir is a conventional reservoir.

The first sample is associated with a first depth of a wellbore and the second sample is associated with a second depth of the wellbore, with the second depth being different than the first depth.

The first sample is associated with a first location and the second sample is associated with a second location that is laterally offset from the first location.

Pulverizing the sample.

Pulverizing the sample comprises either vibrating the sample or striking the sample.

Scanning the sample.

Lowering the temperature of the sample and wherein the fluid is a solvent.

Receiving data relating to the volume of the sample; wherein data relating to the extracted hydrocarbon is the volume of the extracted hydrocarbon.

The sample is one of a plurality of samples; and wherein the method further includes accommodating each of the plurality of samples; submerging at least a portion of each of the plurality of samples in the fluid; lowering the pressure within the pressure chamber to extract a hydrocarbon from each of the plurality of samples; and identifying data relating to the extracted hydrocarbon from each of the plurality of samples; and wherein estimating the reserve of the reservoir comprises using the data relating to the extracted hydrocarbon from each of the plurality of samples.

Data relating to the extracted hydrocarbon is a volume of extracted hydrocarbon.

Using the volume of extracted hydrocarbon to identify a hydrocarbon saturation ratio.

Identifying an average hydrocarbon saturation ratio using the hydrocarbon saturation ratio for each of the plurality of samples.

Receiving data associated with the volume of the reservoir.

Estimating a reserve of a reservoir using the average hydrocarbon saturation ratio and the volume of the reservoir.

Thus, a reservoir reserve estimation assembly has been described. Embodiments of the assembly may generally include a pressure chamber sized to accommodate a sample associated with a reservoir that has a reserve; a first fluid chamber fluidically coupled to the pressure chamber and having a first fluid disposed therein; a second fluid chamber fluidically coupled to the pressure chamber and having a second fluid disposed therein; a hydrocarbon analyzer fluidically coupled to the pressure chamber; and a vacuum device fluidically coupled to the pressure chamber. For any of the foregoing embodiments, the assembly may include any one of the following elements, alone or in combination with each other:

The reservoir reserve estimation assembly is connectable to a drill string.

At least one of a nuclear magnetic resonance scanner and a computed tomography scanner disposed in proximity to the pressure chamber.

A cooling device disposed in proximity to the pressure chamber.

A pulverizing device disposed in proximity to the pressure chamber.

Thus, a method for estimating an available reserve of a reservoir using a downhole operation has been described. Embodiments of the method may generally include isolating a first sample associated with the reservoir and simulating the downhole operation using the first sample; extracting a hydrocarbon from the first sample associated with the reservoir; identifying first data relating to the extracted hydrocarbon from the first sample; isolating a second sample associated with the reservoir and simulating the downhole operation using the second sample; extracting a hydrocarbon from a second sample associated with the reservoir; identifying second data relating to the extracted hydrocarbon from the second sample; and estimating the available reserve of a reservoir using the downhole operation using the first data and the second data. For any of the foregoing embodiments, the method may include any one of the following, alone or in combination with each other:

The downhole operation is hydraulic fracturing.

The first data is the volume of the extracted hydrocarbon from the first sample.

The second data is the volume of the extracted hydrocarbon from the second sample.

The foregoing description and figures are not drawn to scale, but rather are illustrated to describe various embodiments of the present disclosure in simplistic form. Although various embodiments and methods have been shown and described, the disclosure is not limited to such embodiments and methods and will be understood to include all modifications and variations as would be apparent to one skilled in the art. Therefore, it should be understood that the disclosure is not intended to be limited to the particular forms disclosed. Accordingly, the intention is to cover all modifications, equivalents and alternatives falling within the spirit and scope of the disclosure as defined by the appended claims.

What is claimed is:

1. A method for estimating a reserve of a reservoir, the method comprising:

isolating a first sample associated with the reservoir;
extracting a hydrocarbon from the first sample associated with the reservoir;
identifying first data relating to the extracted hydrocarbon from the first sample;
isolating a second sample associated with the reservoir;
extracting a hydrocarbon from a second sample associated with the reservoir;
identifying second data relating to the extracted hydrocarbon from the second sample; and
estimating the reserve of the reservoir using the first data and the second data,
wherein isolating the first sample comprises:
    submerging at least a portion of the first sample in a fluid; and
    disposing the first sample and the fluid in a pressure chamber.

2. The method of claim 1,
wherein each of the first sample and the second sample is a core sample or a core plug; and
wherein isolating the second sample comprises:
    submerging at least a portion of the second sample in the fluid; and
    disposing the second sample and the fluid in the pressure chamber.

3. The method of claim 2, further comprising lowering the temperature of the first sample and the second sample and wherein the fluid is a solvent.

4. The method of claim 2,
wherein extracting a hydrocarbon from the first sample comprises:
    purging the pressure chamber with an inert gas; and
    applying a vacuum force to the first sample; and
wherein extracting a hydrocarbon from the second sample comprises:
    purging the pressure chamber with the inert gas; and
    applying a vacuum force to the second sample.

5. The method of claim 4, further comprising scanning the first sample and the second sample before and after the hydrocarbons are extracted from the first sample and the second sample.

6. The method of claim 4, further comprising pulverizing the first sample and the second sample.

7. The method of claim 6, wherein pulverizing the first sample and the second sample comprises vibrating the first sample and the second sample.

8. The method of claim 6, wherein pulverizing the first sample and the second sample comprises striking the first sample and the second sample with a plurality of projectiles.

9. The method of claim 1, wherein the reservoir is an unconventional reservoir.

10. The method of claim 1, wherein the reservoir is a conventional reservoir.

11. The method of claim 1, wherein the first sample is associated with a first depth of a wellbore and the second sample is associated with a second depth of the wellbore, with the second depth being different than the first depth.

12. The method of claim 1, wherein the first sample is associated with a first location and the second sample is associated with a second location that is laterally offset from the first location.

13. A method of estimating a reserve of a reservoir, the method comprising:
accommodating a sample obtained from a reservoir having a reserve in a pressure chamber;
submerging at least a portion of the sample in a fluid;
filling the pressure chamber with a gas;
lowering the pressure within the pressure chamber to extract a hydrocarbon from the sample;
identifying data relating to the extracted hydrocarbon; and
estimating the reserve of the reservoir using the data relating to the extracted hydrocarbon.

14. The method of claim 13,
wherein the sample is a core sample or a core plug; and
wherein the method further comprises pulverizing the sample.

15. The method of claim 14, wherein pulverizing the sample comprises either vibrating the sample or striking the sample.

16. The method of claim 13, further comprising scanning the sample.

17. The method of claim 13, further comprising lowering the temperature of the sample and wherein the fluid is a solvent.

18. The method of claim 13, wherein the reservoir is an unconventional reservoir.

19. The method of claim 13, wherein the reservoir is a conventional reservoir.

20. The method of claim 13, further comprising receiving data relating to the volume of the sample;
wherein data relating to the extracted hydrocarbon is the volume of the extracted hydrocarbon.

21. The method of claim 13,
wherein the sample is one of a plurality of samples; and
wherein the method further comprises:
    accommodating each of the plurality of samples;
    submerging at least a portion of each of the plurality of samples in the fluid;
    lowering the pressure within the pressure chamber to extract a hydrocarbon from each of the plurality of samples; and
    identifying data relating to the extracted hydrocarbon from each of the plurality of samples; and
wherein estimating the reserve of the reservoir comprises using the data relating to the extracted hydrocarbon from each of the plurality of samples.

22. A reservoir reserve estimation assembly comprising:
a pressure chamber sized to accommodate a sample associated with a reservoir that has a reserve;
a first fluid chamber fluidically coupled to the pressure chamber and having a first fluid disposed therein;
a second fluid chamber fluidically coupled to the pressure chamber and having a second fluid disposed therein;
a hydrocarbon analyzer fluidically coupled to the pressure chamber; and
a vacuum device fluidically coupled to the pressure chamber;
wherein the pressure chamber is configured to receive the first fluid from the first fluid chamber while accommodating the sample.

23. The reservoir reserve estimation assembly of claim 22, wherein the reservoir reserve estimation assembly is connectable to a drill string.

24. The reservoir reserve estimation assembly of claim 22, further comprising at least one of a nuclear magnetic resonance scanner and a computed tomography scanner disposed in proximity to the pressure chamber.

25. The reservoir reserve estimation assembly of claim 22, further comprising a cooling device disposed in proximity to the pressure chamber.

26. The reservoir reserve estimation assembly of claim 22, further comprising a pulverizing device disposed in proximity to the pressure chamber.

* * * * *